United States Patent [19]

Johnson et al.

[11] 4,071,622

[45] Jan. 31, 1978

[54] TREATMENT OF A MAMMARY OR DMBA INDUCIBLE TUMOR

[75] Inventors: Edwin Samuel Johnson, Antioch; John Hunter Seely, Lake Forest, both of Ill.

[73] Assignee: Abbott Laboratories, North Chicago, Ill.

[21] Appl. No.: 657,344

[22] Filed: Feb. 11, 1976

[51] Int. Cl.² ........................................... A61K 37/02
[52] U.S. Cl. .................................................. 424/177
[58] Field of Search .......................................... 424/177

*Primary Examiner*—Jerome D. Goldberg
*Attorney, Agent, or Firm*—Paul D. Burgauer; Robert L. Niblack

[57] ABSTRACT

Certain nonapeptide amides were found which, upon administration at daily dosages of from about 1–200 μg/kg to warm-blooded animals, cause regression of DMBA-inducible or mammary tumors without causing adverse effects on healthy tissues.

9 Claims, No Drawings

TREATMENT OF A MAMMARY OR DMBA INDUCIBLE TUMOR

DETAILED DESCRIPTION OF THE INVENTION

For a number of years there has been a search for substances that, upon administration to warm-blooded animals, will cause the regression and/or elimination of mammary or DMBA-inducible tumors without causing substantial adverse effect to healthy tissue of the host.

It has now been found that a series of closely related peptides have the ability to interfere with the metabolism of DMBA-inducible or mammary tumors to the point of drastically impairing their cell growth which, in turn, leads to said tumor's regression and oftentimes, to the elimination of said tumor all together.

The principal object of the present invention is, therefore, to provide a treatment for warm-blooded animals that carry one or more active mammary or DMBA-inducible tumors or neoplasias; it is a more particular object of this invention to provide a chemical treatment for warm-blooded animals afflicted with DMBA-inducible or mammary tumor growth which reduces the size of said tumor without adverse effect to the host.

These and other objects are accomplished by administering to a warm-blooded animal, carrying a growing mammary or DMBA-inducible tumor, an effective daily dose of a nonapeptide of the formula

I.

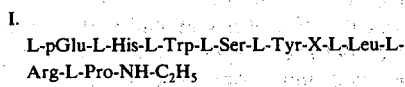

L-pGlu-L-His-L-Trp-L-Ser-L-Tyr-X-L-Leu-L-Arg-L-Pro-NH-C$_2$H$_5$ wherein X denotes the optically active D-form of an aminoacid of the formula -NH-CHR'-CO- with R' being benzyl, 3-indolyl or p-hydroxy-benzyl. The divalent radical X thus represents D-phenylalanyl, D-tryptophyl and D-tyrosyl.

In a general embodiment, the above nonapeptide is administered to a warm-blooded animal carrying a tumor of the above type at a parenteral dose of between 1 and 200 μg/kg/day as a single daily dose or divided into 2-4 daily doses of the correspondingly smaller amounts. Where oral administration is desired, the dose range is between 2 and 500 μg/kg/day and can easily be exceeded since the compound of formula I does not show any toxic effects at oral doses 100 mg/kg or more. The above reference to "parenteral" is intended to include all routes of administration other than oral; it is particularly directed to intramuscular, subcutaneous, intravenous by injection or infusion, intra-vaginal, by suppository, by nasal drops, etc. For these formulations, solutions of I at a concentration of 5-100 μg/ml in 0.9% saline provide an excellent dosage form. If desired, small amounts of albumin may be added to prevent adsorption of I to the glass container in which this dosage form is prepared or stored.

The compound of formula I is highly water-soluble; it can be stored for essentially indefinite periods of time as a solid or as a solution in water or saline. Of course, where desired, buffers such as tris(hydroxymethyl)aminomethane or other pharmaceutically acceptable additives may be included in the solutions before storage or before use.

For oral preparations, any number of pharmaceutical forms can be used, e.g., syrups, elixirs, suspensions or the compound can be processed into wafers, pills, tablets and the like. However, since the dosage required is extremely small, the usual tableting methods require the use of fillers and other excipients to prepare tablets of manageable size. In a preferred embodiment, the oral dosage form consists of a tablet containing between 0.1 and 5.0 mg. of the above peptide per tablet. Such tablets can be coated in the usual fashion, preferably using a readily soluble coating material, e.g., sugar, etc. or the above amount can be incorporated into gelatin capsules which promptly dissolve upon introduction into the stomach. In any event, the usual flavoring and coloring agents can be used without effect on the active peptide so incorporated.

Tablets of this type are prepared in the usual fashion by compounding the active ingredient with starch, granulating the mixture and, after adding the necessary fillers, flavoring agents, lubricants, etc., the mixture is slugged and passed through a 30 -mesh screen. The thoroughly blended mixture is then compressed into tablets of desired hardness with the usual punch, preferably to make bisected tablets for easier b.i.d. administration.

In order to show the preparation and use of the compounds of the present invention, reference is made to the following examples which, however, are not intended to limit the invention in any respect.

EXAMPLE 1

Proline carrying as a blocking group the t-butyloxycarbonyl substituent (elsewhere herein referred to as Boc-) on the amino group is esterified by combining it with a chloromethylated divinylbenzene-styrene copolymer (marketed by Bio-Rad as Merrifield resin) containing 2% of cross linking, using the method described by Stewart, et al. in "SOLID PHASE PEPTIDE SYNTHESIS", (published in 1969 by Freeman & Company), San Francisco, (page 1). In this manner, a resin is produced which by hydrolysis and aminoacid analysis shows to contain 0.47 millimoles of proline/g. of resin. In an automatic synthesizer developed according to the previously cited Merrifield apparatus, 4.6 g. of this resin/aminoacid material is used for the synthesis of the desired nonapeptide. Each N-blocked aminoacid is added in a three-fold access and allowed to couple to the existing aminoacid-resin ester in the usual coupling cycle. The coupling reaction is carried out for 4.5 hours with continuous shaking and the reaction is subsequently washed six times with methanolchloroform 1.2 for 1.5 minutes each and 4 times with ethanol for 1.5 minutes each. In each instance, a total volume of 48 milliliters is used and the drain time after shaking usually is about 1.5 minutes.

After coupling, the mixture is washed four times for 1.5 minutes each with dioxane, twice with 4N hydrochloric acid/dioxane for five minutes and twenty-five minutes, respectively, five times with dioxane for 1.5 minutes each, three times with ethanol for 3 minutes each, three times with chloroform for 1.5 minutes each, three times with 10% triethylamine/chloroform for 1.5 minutes each, four times with chloroform for 1.5 minutes each and six times with dichloromethane for 1.5 minutes each. Ordinarily the solvent used for the coupling reaction is dichloromethane or, when the solubility of the blocked aminoacid is low, a mixture of dichloromethane and dimethylformamide. Coupling is effected by the addition of a solution of dicyclohexylcarbodiimide in diichloromethane at a 2.9 fold excess.

The sequence used for deprotection, neutralization and coupling of the next aminoacid is done in a fully automatic system as described above. In this manner, the peptide is assembled using in turn Boc-Arg(Tos), Boc-Leu, Boc-D-Trp, Boc-Tyr(Cl$_2$Bzl), Boc-Ser(Bzl), Boc-Trp, Boc-His(DNP), and pGlu wherein all aminoacids are in the L-form except in the case of tryptophane.

The resin is removed from the vessel and suspended in 200 ml. of 5% triethylamine/methanol and 100 ml. of distilled ethylamine is added thereto. After 24 hours, the resin is removed by filtration and the solution evaporated to yield a solid. The solid is taken up in glacial acetic acid and applied to a 3 × 50 cm. column of silica gel equilibrated with 5% methanol/chloroform.

The column is eluted with 5% methanol in chloroform until all traces of N-ethyl dinitroaniline, the yellow by-product of the histidine protecting group DNP is removed. The eluant is then changed to 33% methanol/chloroform and fractions of about 30 ml. each are collected. The compound is located by thin-layer chromatography of aliquots of the fractions (Silica gel G. 33% MeOH/CHCl$_3$, Cl$_2$/tolidine spray). The fractions containing the product are pooled and evaporated to give a solid which is precipitated from methanol with ether. This tri-protected nonapeptide (protective groups at Ser, Tyr and Arg) is thus obtained in an amount of 1.69 g., representing an overall yield of 43% of theory.

A 250 mg. sample of the above is placed in a hydrogen fluoride reaction vessel with 250 mg. of anisole and about 5 ml. of anhydrous hydrogen fluoride is distilled into it. After 1 hour at 0° C., the hydrogen fluoride is removed in vacuo, and the residue is taken up in 1% acetic acid. This solution is extracted with ether, and the aqueous phase applied to a 1 × 30 cm. column of a highly basic ion exchange resin (marketed by Bio-Rad as AG1 × 2 resin) in the acetate form. The product is eluted with 0.1 N acetic acid and localized using thin-layer chromatography (CHCl$_3$/MeOH/32% HOAc: 120/90/40, Silica gel G.,Cl$_2$/tolidine). The product bearing solution is lyophilized, rechromatographed on a Sephadex G-25 ® (marketed by Pharmacia of Uppsala, Sweden) column. The product eluted is collected and lyophilized to yield a fluffy white solid in a 25% overall yield.

When in the above synthesis, the Boc-D-Trp (yielding Compound A) is replaced by Boc-D-Tyr(Cl$_2$B$_2$l) (yielding Compound B) or Boc-D-phenyl-alanine (yielding Compound C), the above synthesis proceeds in the same fashion, again in all instances, using the automatic synthesizer described above. In all instances, the nonapeptides are identified by amino acid analysis and nmr-spectrum which confirm the presence of the assembled aminoacids in the expected molecular ratio.

EXAMPLE 2

In a group of 3 female, 50-day old rats, tumors were induced by intragastric feeding of 20 mg of 7,12-dimethylbenzanthracene (DMBA) in 2 ml. of sesame oil. The animals developed tumors within 10–12 weeks. All animals were maintained on normal rations for 100 days following the DMBA administration, at which time treatment with the compound identified as Compound A was started, using a b.i.d. regimen for 11 days, 20 μg/day, the compound being administered subcutaneously dissolved in isotonic saline containing 0.1% (wt/vol.) of bovine serum albumin.

The three animals carried a total of 7 tumors at the beginning of the treatment with a total volume of 39.2 cc. After 3 days, the 7 tumors had reduced to a volume of 26.7 cc; on day 6 the volume had reduced to 18.6 cc, on day 10 it was 8.7 cc, which was also the volume upon sacrifice of the animals on day 11. One of the animals which started with only two tumors of a total volume of 11.65 cc showed a volume of 7.5, 8.1, 3.8 and 3.76 cc on the above days of measurement or a total volume reduction of 67.7%.

EXAMPLE 3

The animals were prepared and pre-treated in the same fashion as those in Example 2, but Compound B was used for the 11-day treatment. The three rats used started the regimen with a total of 7 tumors of 43.3 cc total volume. Again, the tumor volumes were measured on days 3, 6, 10 and upon sacrifice, showing 37.5, 24.9, 16.3 and 15.0 cc respectively. In one specific animal starting with one tumor only, the 3.6 cc tumor reduced to 2.5, 1.33, 0.73 and 0.125 cc respectively on the days indicated, i.e., a total reduction of 96.5%.

EXAMPLE 4

Except for the use of Compound C, all steps of the preceding two examples were repeated. The total of 13.4 cc of volume of 3 tumors in two rats was reduced to 10.1, 5.4, 6.4 and 5.5 cc on days 3, 6, 10 and 11. The increase noted on the total tumor volume on day 10 was due to one single tumor in one animal which spontaneously increased between days 6 and 10 from 0.38 to 4.6 cc. However, that tumor was found reduced to 3.0 cc on day 11. A third animal treated in the same fashion started out the regimen with 4 tumors of 28.1 cc which reduced to 15 cc by day 6. The animal died thereafter of causes diagnosed as having no connection with the tumors or the treatment (chronic murine pneumonia).

As demonstrated above, the treatment with the compounds of formula I produces drastic regression of DMBA-induced tumors. This effect is in acknowledged close relationship with the treatment of mammary tumors for which the DMBA-induced tumors are used as models (see "Pathology of Tumours in Laboratory Animals", Vol. 1, p. 31, issued by the International Agency for Research on Cancer; Lyon 1973). Thus, the above defined narrow class of compounds can be used for the amelioration of mammary or DMBA-inducible tumors, the eventual elimination of said tumors upon prolonged treatment as well as the extension of the host's survival rate. Since these compounds have essentially no toxicity even in doses of 100 mg/kg, and since the doses to be used for successful treatment in animals are in the μg/kg levels, the therapeutic index of the compounds is extremely high. This makes the above treatment an important and unexpected discovery and valuable addition to the field of tumor treatments.

We claim:

1. The method of reducing the size of a mammary or DMBA-inducible tumor in a warm-blooded animal by administering to an animal having a mammary or DMBA-inducible tumor an effective daily amount to reduce the size of such a tumor of a nonapeptide of the formula L-pGlu-L-His-L-Trp-L-Ser-L-Tyr-X-L-Leu-L-Arg-L-Pro-NH-C$_2$H$_5$ wherein X denotes the optically active D-form of Tyr, Trp or Phe.

2. The method of claim 1 wherein X is tyrosyl.
3. The method of claim 1 wherein X is tryptophyl.
4. The method of claim 1 wherein X is phenylalanyl.
5. The method of claim 1 wherein said tumor is a mammary tumor.
6. The method of claim 1 wherein said tumor is a DMBA-inducible tumor.
7. The method of claim 1 wherein said nonapeptide is administered at a daily parenteral dose of between 1 and 200 µg/kg.
8. The method of claim 7 wherein said parenteral dose is administered as solution in 0.9% of saline.
9. The method of claim 1 wherein said nonapeptide is administered at a daily oral dose of between 2 and 500 µg/kg.

* * * * *